(12) United States Patent
Park

(10) Patent No.: US 9,792,469 B1
(45) Date of Patent: Oct. 17, 2017

(54) WIRELESS PHYSICAL PROPERTY SENSOR WITH DIGITAL COMMUNICATIONS

(71) Applicant: PACESETTER, INC., Sylmar, CA (US)

(72) Inventor: Jin Woo Park, Suwanee, GA (US)

(73) Assignee: PACESETTER, INC., Sylmar, CA (US)

( * ) Notice: Subject to any disclaimer, the term of this patent is extended or adjusted under 35 U.S.C. 154(b) by 0 days.

(21) Appl. No.: 15/295,790

(22) Filed: Oct. 17, 2016

(51) Int. Cl.
  *G08B 1/08* (2006.01)
  *G06K 7/10* (2006.01)
(52) U.S. Cl.
  CPC ..... *G06K 7/10029* (2013.01); *G06K 7/10069* (2013.01)
(58) Field of Classification Search
  CPC ................ G06K 7/10029; G06K 7/10069
  See application file for complete search history.

(56) References Cited

U.S. PATENT DOCUMENTS

| 9,457,627 | B1* | 10/2016 | Keller | B60C 23/0479 |
| 2003/0120150 | A1* | 6/2003 | Govari | A61B 5/0031 |
| | | | | 600/424 |
| 2004/0011365 | A1* | 1/2004 | Govari | A61B 17/1707 |
| | | | | 128/899 |
| 2017/0123096 | A1* | 5/2017 | Wilson | G01V 3/28 |

* cited by examiner

*Primary Examiner* — Erin File

(57) ABSTRACT

The present disclosure provides systems and methods implemented using physical property sensors. A physical/property sensor includes a sensor coil configured to wirelessly communicate with an external interrogator, an analog front end communicatively coupled to the sensor coil, a microcontroller communicatively coupled to the analog front end, and a physical property sensing element, wherein the microcontroller is configured to generate a digitally modulated electrical signal based on signals generated by the physical property sensing element, and wherein the analog front end is configured to forward the digitally modulated electrical signal to the sensor coil for transmission to the external interrogator.

16 Claims, 5 Drawing Sheets

WIRELESS PHYSICAL PROPERTY SENSOR WITH DIGITAL COMMUNICATIONS

FIELD OF THE DISCLOSURE

The present disclosure relates generally to monitoring physical properties, and more particularly to systems and methods using wireless physical property sensors having digital communication capabilities.

BACKGROUND ART

Wireless physical property sensors may be implanted in a patient to monitor one or more physical properties of the patient. For example, a pressure sensor may be implanted in a patient to monitor pulmonary artery pressure of the patient. At least some known implanted wireless physical property sensors operate based on a LC resonant principle. Specifically, the electrical resonant frequency of the sensor is a function of the sensed physical property (e.g., pressure). Accordingly, as the sensed physical property changes, the resonant frequency also changes. To determine the resonant frequency of the wireless sensor, an external interrogator device monitors the wireless sensor using a relatively sophisticated electronics architecture, which may be relatively expensive. Further, such sensors generally include electrically passive components to generate analog signals, and are capable delivering limited amounts of information. For example, such sensors may only provide values for the sensed physical property.

BRIEF SUMMARY OF THE DISCLOSURE

In one embodiment, the present disclosure is directed to a physical property sensor. The physical property sensor includes a sensor coil configured to wirelessly communicate with an external interrogator, an analog front end communicatively coupled to the sensor coil, a microcontroller communicatively coupled to the analog front end, and a physical property sensing element, wherein the microcontroller is configured to generate a digitally modulated electrical signal based on signals generated by the physical property sensing element, and wherein the analog front end is configured to forward the digitally modulated electrical signal to the sensor coil for transmission to the external interrogator.

In another embodiment, the present disclosure is directed to a communication system. The communication system includes an external interrogator, and a physical property sensor. The physical property sensor includes a sensor coil configured to wirelessly communicate with the external interrogator, an analog front end communicatively coupled to the sensor coil, a microcontroller communicatively coupled to the analog front end, and a physical property sensing element, wherein the microcontroller is configured to generate a digitally modulated electrical signal based on signals generated by the physical property sensing element, and wherein the analog front end is configured to forward the digitally modulated electrical signal to the sensor coil for transmission to the external interrogator.

In another embodiment, the present disclosure is directed to a method for managing communications between an external interrogator and a plurality of physical property sensors. The method includes transmitting a request from the external interrogator to the plurality of physical property sensors, receiving, in response to the request, responses from the plurality of physical property sensors, each response received in accordance with a randomly generated communication parameter, determining, at the external interrogator, whether responses have been received from each of the plurality of physical property sensors without data collision, assigning a unique communication parameter to each of the plurality of physical property sensors when responses have been received from each of the plurality of physical property sensors without data collision, and receiving data from the plurality of physical property sensors in accordance with the assigned communication parameters.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings.

DETAILED DESCRIPTION OF THE DISCLOSURE

The systems and methods described herein provide a wireless physical property sensor that includes a microcontroller or equivalent state machine and a non-volatile memory. The sensor further includes a transmitter capable of sending sensor data and additional data (e.g., a sensor/patient ID, a mathematical calibration code, etc.) using digital communication. The data receiving capabilities and non-volatile memory of the sensor described herein facilitate receiving and storing pertinent information using a modified front end. In the systems and methods described herein, the sensor uses digital communications to transmit and receive data. Digital communications may include, for example, single frequency on-off keying (OOK), two frequency binary frequency-shift-keying (FSK), and/or phase-shift-keying (PSK) modulation.

An anti-data collision communication scheme is also provided. The anti-data collision communication scheme facilitates preventing data collisions when multiple sensors are interrogated and energized simultaneously. This allows multiple sensors to be successfully interrogated simultaneously.

Figure 1:
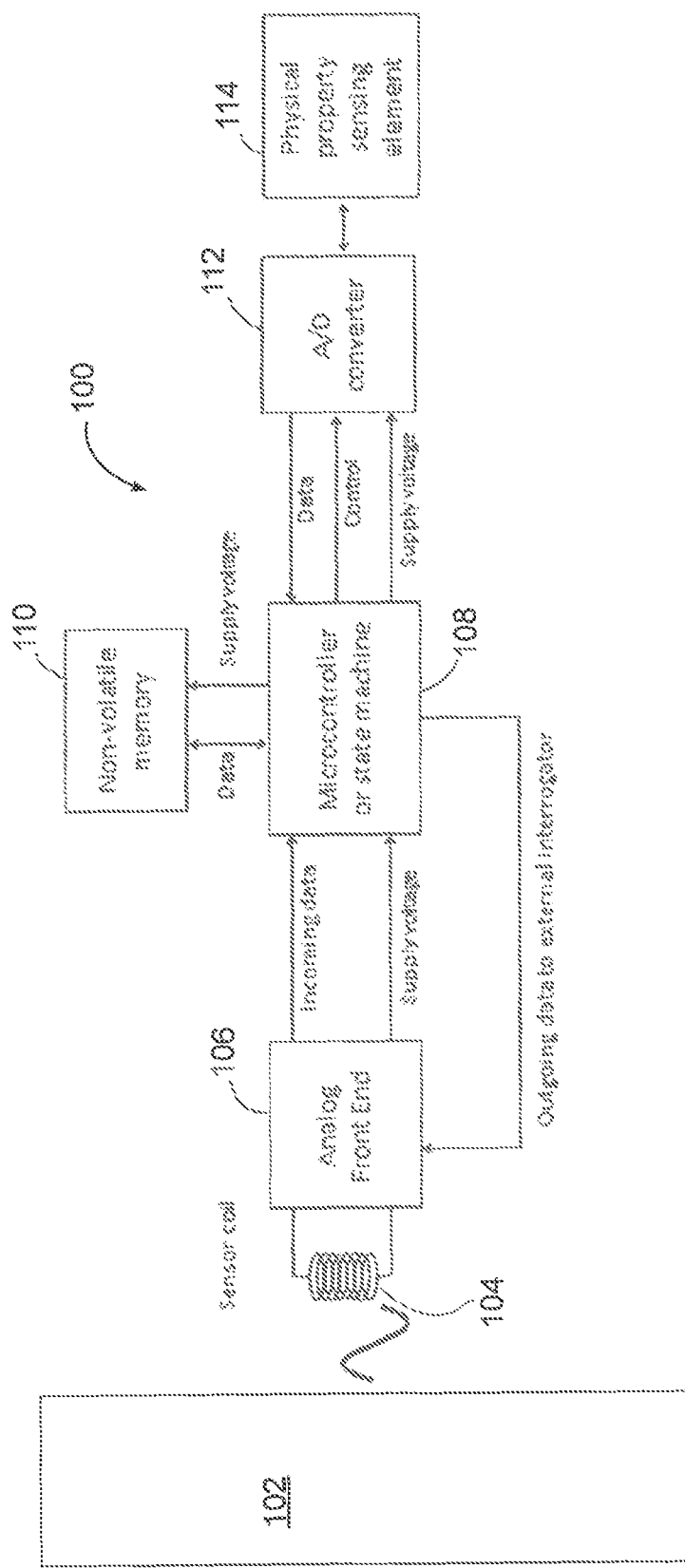
FIG. 1 is a block diagram of a communication system including a wireless physical property sensor.

Referring now to the drawings, and in particular to FIG. 1, a wireless physical property sensor is indicated generally at 100. Sensor 100 senses a physical property of an environment in which sensor 100 is located. For example, sensor 100 may sense a pressure, temperature, SvO2 content, and/or stress of the environment. The value of the sensed physical property may be transmitted to an external interrogator 102. Sensor 100 may be implanted within a patient to monitor at least one physical property within the patient and transmit the monitored physical property to external interrogator 102.

In this embodiment, sensor 100 includes a sensor coil 104, an analog front end 106, a microcontroller (MCU) 108 (or equivalent state machine), a non-volatile memory 110, an analog to digital (A/D) converter 112, and a sensing element 114. Sensor coil 104 facilitates communications between sensor 100 and external interrogator 102 by transmitting and receiving electrical signals through a coupling with an antenna (not shown) of external interrogator 102.

Analog front end 106 is coupled to sensor coil 104. In this embodiment, analog front end 106 harvests and stores energy received from external interrogator 102 and supplies that energy as a supply voltage to MCU 108 to power sensor 100. Analog front end 106 also forwards incoming data to MCU 108, and retrieves digital data from MCU 108 for sensor coil 104 to transmit to external interrogator 102.

A/D converter 112 is coupled to sensing element 114 and converts analog signals from sensing element 114 into digital data. That digital data is sent to MCU 108 for storing in non-volatile memory and/or for transmission by sensor coil 104. Sensing element 114 may be, for example, a capacitor capable of sensing a pressure in the environment where sensor 100 is located. Non-volatile memory 110 stores data received from external interrogator 102 and data from sensing element 114. Non-volatile memory 110 may also store, for example, a sensor ID (e.g., an alphanumeric string uniquely identifying sensor 100), a unique transducer characteristic of sensor 100, and/or calibration information for sensor 100 used to calculate the physical property being measured. Non-volatile memory 110 may also store instructions for implementing an anti-collision scheme, as described below.

In this embodiment, MCU 108 generates an electrical signed modulated digitally and including data requested by external interrogator 102 (e.g., information stored in non-volatile memory 110 and/or data acquired by sensing element 114). The digitally modulated electrical signal is received by analog front end 106 for transmission.

Figure 2:
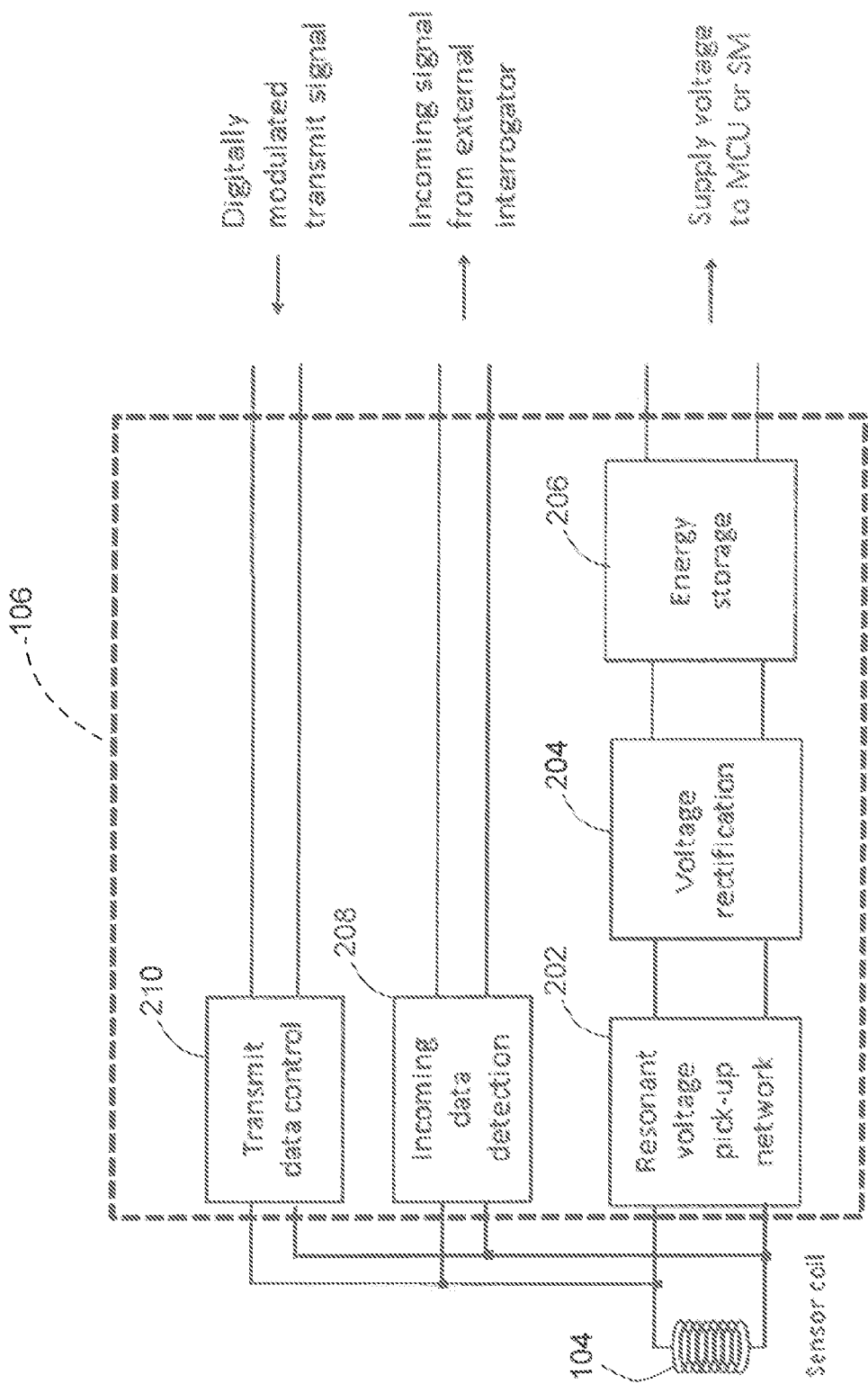
FIG. 2 is a block diagram of a sensor coil and an analog front end that may be used with the wireless physical property sensor shown in FIG. 1.

FIG. 2 is a block diagram of sensor coil 104 and analog front end 106. As shown in FIG. 2, to provide the supply voltage to MCU 108, analog front end 106 includes, in series, a resonant voltage pick-up network 202, a voltage rectification unit 204, and an energy storage unit 206. Resonant voltage pick-up network 202 may include, for example, a capacitor. Voltage rectification unit 204 includes diodes that convert AC voltage to DC voltage. Energy storage unit 206 may include a rechargeable battery or capacitor to store energy received from sensor coil 104. Energy storage unit 206 may, for example, provide the stored energy to MCU 108 to power MCU 108.

In this embodiment, analog front end 106 also includes an Incoming data detection unit 208 that retrieves incoming digital data from sensor coil and provides it to MCU 108. Incoming data detection unit 208 may include, for example, an envelope detector. Analog front end 106 also includes a transmit data control unit 210 for supplying digitally modulated electrical signals from MCU 108 to sensor coil 104 for transmission to external interrogator 102.

In some embodiments, multiple sensors 100 are interrogated by external interrogator 102 substantially simultaneously. Accordingly, more than one sensor 100 may attempt communication with external interrogator 102 at the same time, and an anti-collision scheme may be implemented to prevent communications for one sensor 100 from interfering with communications for other sensors 100, as described herein.

Figure 3:
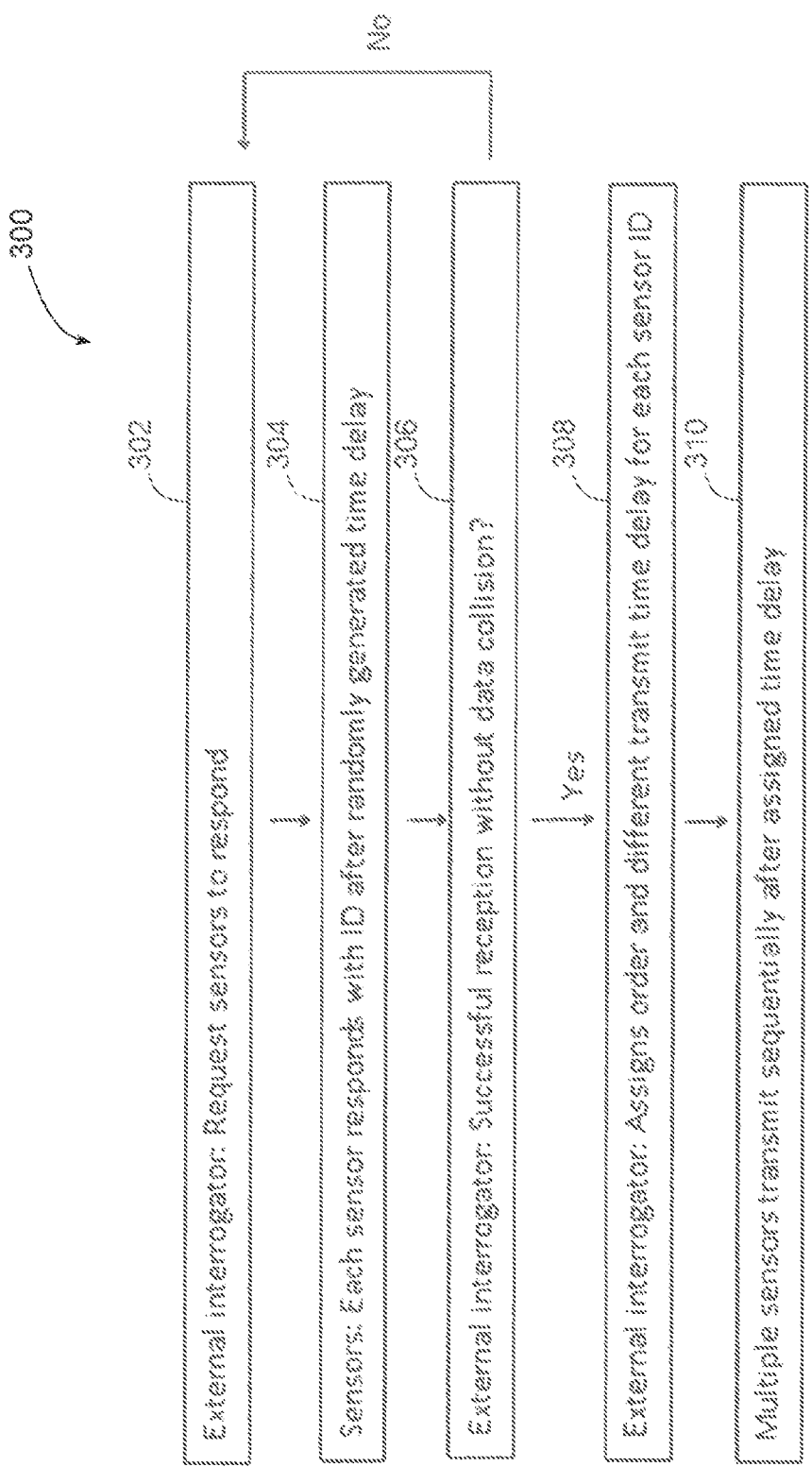
FIG. 3 is a flow chart of one embodiment of a method implementing a single channel anti-collision scheme that may be used with the system shown in FIG. 1.

FIG. 3 is a flow chart of one embodiment of a method 300 implementing a single channel anti-collision scheme. In method 300, all sensors communicate with an external interrogator over a single communication channel, but at different times. At block 302, an external interrogator, such as external interrogator 102 (shown in FIG. 1), requests sensors, such as sensors 100 (shown in FIG. 1), to respond to the external interrogator. At block 304, each sensor responds with an associated sensor ID. Further, each sensor responds after a randomly generated time delay. That is, each sensor receives the request from the external interrogator, randomly generates a time delay, and then responds after the time delay passes.

At block 306, the external interrogator determines whether it has successfully received responses from all sensors (i.e., whether the sensors all had different time delays). If the external interrogator does not successfully receive responses from all sensors, the flow returns to block 302. If, at block 306, the external interrogator successfully receives responses, the flow proceeds to block 308.

At block 303, the external interrogator formally assigns an order of transmission and transmit time delay to each sensor ID, so that the sensors are able to transmit data on the same frequency channel at different times. The assigned transmit time delays may or may not correspond to the randomly generated time delay. For example, if a first sensor transmits at a time delay of 20 microseconds (µs) and a second sensor transmits at a time delay of 1280 µs, the external interrogator may assign a time delay of 0 µs to the first sensor and 20 µs to the second sensor (e.g., to save time in receiving subsequent data transmissions). At block 310, according to the assigned order of transmission and transmit time delays, the sensors sequentially transmit data to the external interrogator.

Figure 4:
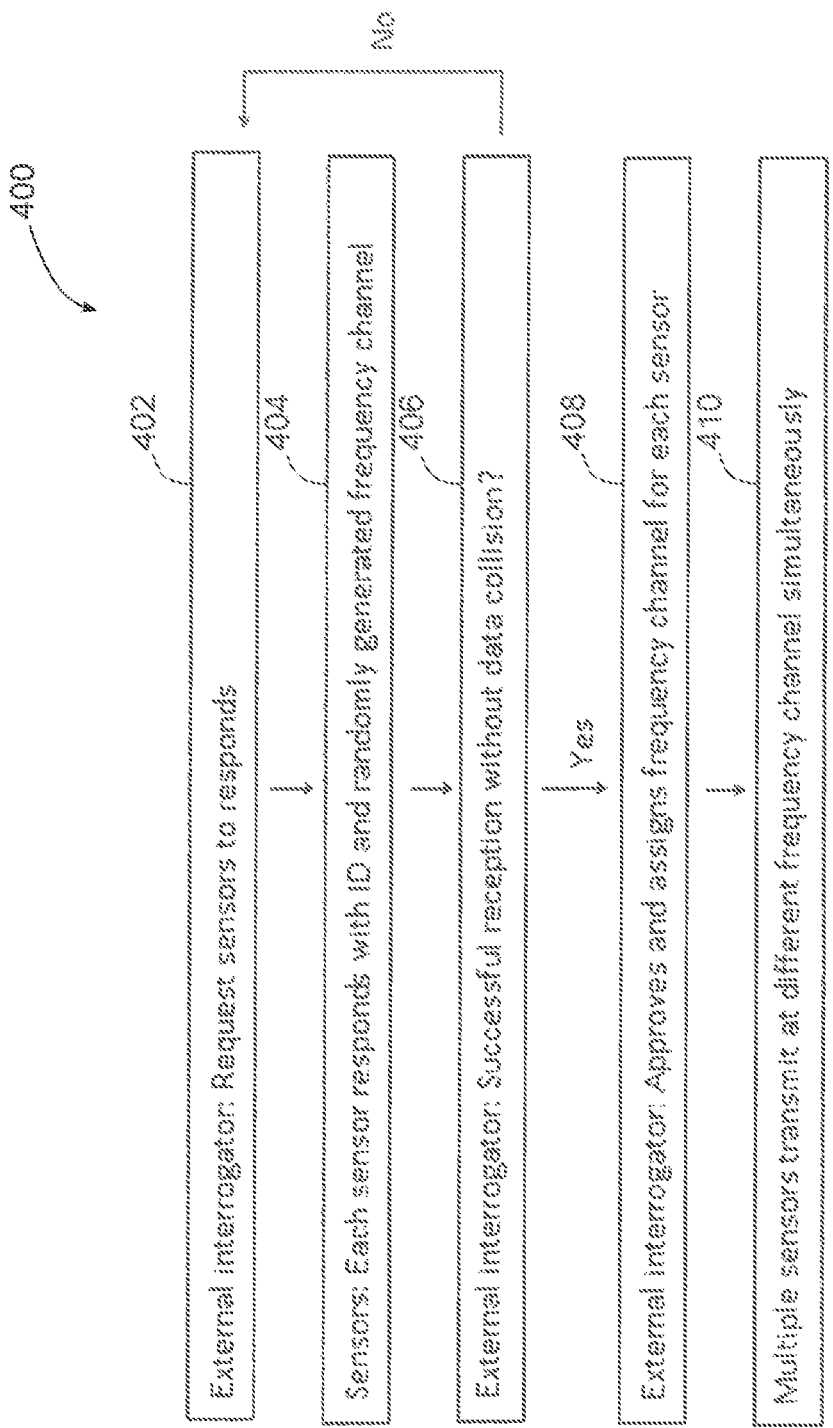
FIG. 4 is a flow chart of one embodiment of a method implementing a multiple channel anti-collision scheme that may be used with the system shown in FIG. 1.

FIG. 4 is a flow chart of one embodiment of a method 400 implementing a multiple channel anti-collision scheme. In method 400, all sensors communicate with an external interrogator over respective communication channels. Accordingly, the sensors can communicate with external interrogator simultaneously.

At block 402, an external interrogator, such as external interrogator 102 (shown in FIG. 1) requests sensors, such as sensors 100 (shown in FIG. 1), to respond to the external interrogator. At block 404, each sensor responds with an associated sensor ID and a randomly generated frequency channel. That is, each sensor receives the request from the external interrogator, randomly generates a frequency channel designation, and then responds using the randomly generated frequency channel.

At block 406, the external interrogator determines whether it has successfully received responses from all sensors (i.e., whether the sensors all had different frequency channels). If the external interrogator does not successfully receive responses from all sensors, the flow returns to block 402. If, at block 406, the external interrogator successfully receives responses, the flow proceeds to block 408.

At block 408, the external interrogator formally approves and assigns frequency channels (i.e., corresponding to the randomly generated frequency channels) to the sensors, so that the sensors are able to transmit data on the different frequency channels simultaneously. At block 410, according to the assigned frequency channels, the sensors transmit data to the external interrogator simultaneously.

Accordingly, in both method 300 and method 400, the sensors respond to the external interrogator with randomly generated communication parameters (e.g., time delays or frequency channels). If the randomly generated communication parameters are all different from one another (i.e., all sensor ID's are identified without data collision), the external interrogator either approves the randomly generated communication parameters or assigns the unique communication parameters for each sensor, and the sensors communicate based on the approved or assigned communication parameters.

In one embodiment, when power is removed from a sensor (e.g., when the power stored by energy storage unit 206 is depleted), the assigned time delay in method 300 or the assigned frequency channel in method 400 is forgotten by the sensor. Alternatively, the assigned time delay or assigned frequency channel may be stored in non-volatile memory 110 for future use.

Notably, methods 300 and 400 do not require any communication between the sensors. Instead, the sensors communicate only with the external interrogator. As the wireless sensors typically have a limited antenna coil size and a limited power availability, transmit signals from the sensors may be relatively weak. Further, for the same reasons (i.e., limited antenna coil size and limited power availability), it may be relatively difficult for sensors to detect signals transmitted by other sensors, in contrast, the external interrogator can amplify and detect sensor signals using readily available power and a relatively large antenna. Further, signals transmitted from the external interrogator to the sensors are relatively strong, and thus easily detected by the sensors. Thus, communication schemes that do not rely on sensor-to-sensor communication, such as methods 300 and 400, are advantageous.

Figure 5:
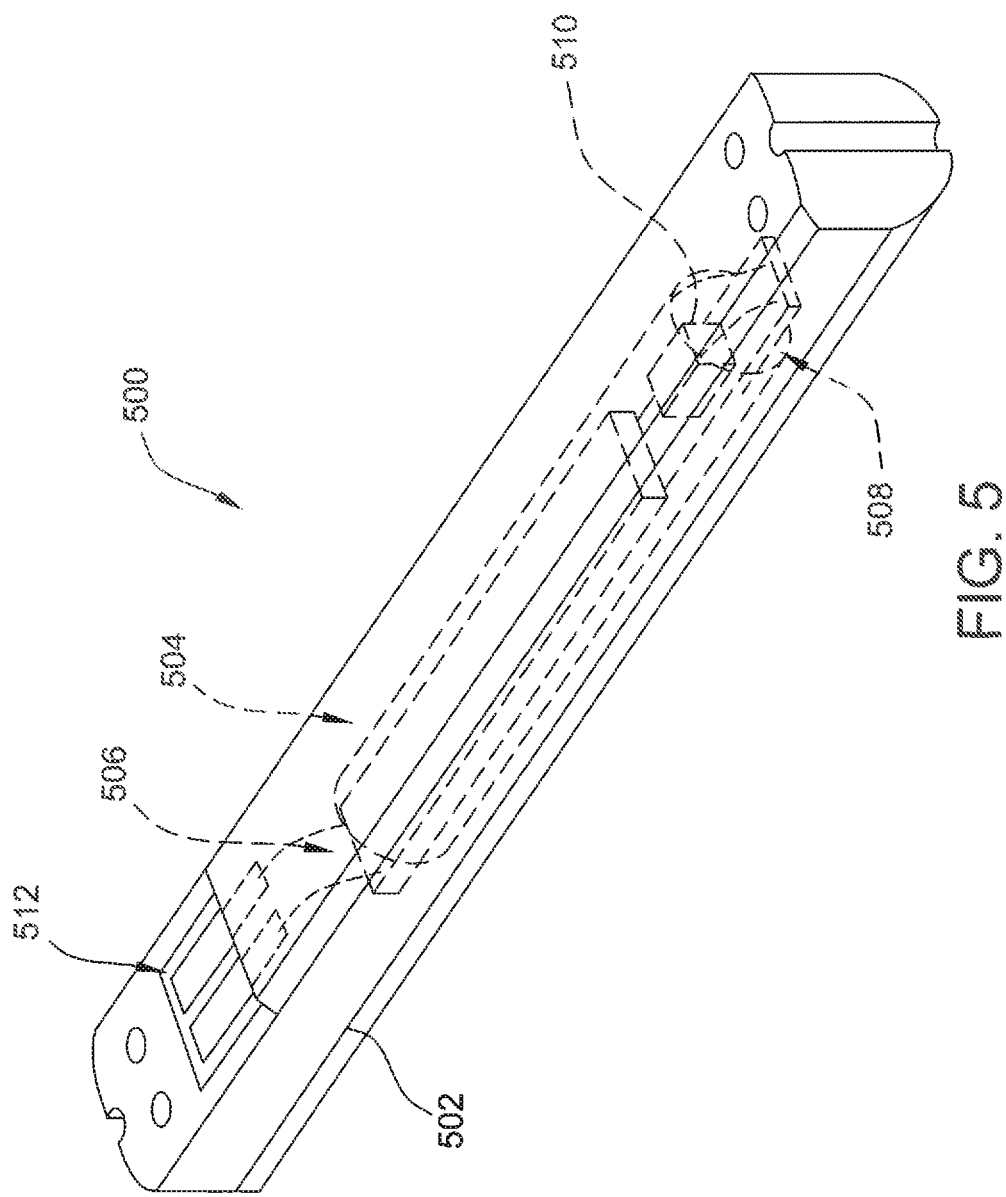
FIG. 5 is a perspective view of one embodiment of a physical property sensor.

FIG. 5 is a perspective view of one embodiment of a physical property sensor 500, such as sensor 100 (shown in FIG. 1). Sensor 500 includes a hermetically-sealed housing 502 that houses a plurality of components. Housing 502 may be made of, for example, fused silica. Housing 502 may be formed using any suitable manufacturing methods.

As shown in FIG. 5, sensor 500 includes a solenoid coil 504. Solenoid coil 504 corresponds to sensor coil 104. To conserve space, in this embodiment, an application-specific integrated circuit (ASIC) chip 506 is positioned within and extends through solenoid coil 504. ASIC chip 506 may include, for example, any of analog front end 106, MCU 108, non-volatile memory 110, or A/D converter 112 (ail shown in FIG. 1). ASIC chip 506 is mounted to a flexible printed circuit board (PCB) 508. Further, an energy storage capacitor 510 (corresponding to energy storage unit 206) may be mounted to flexible PCB 508. Flexible PCB 508 electrically interconnects solenoid coil 504, ASIC chip 506, and energy storage capacitor 510.

In this embodiment, sensor 500 also includes a pressure sensing capacitor 512 (corresponding to physical property sensing element 114). Unlike the other components of sensor 500, at least a portion of pressure sensing capacitor 512 may be exposed to the environment surrounding sensor 500 to facilitate accurately measuring the pressure in the environment. Pressure sensing capacitor 512 is electrically coupled to ASIC chip 506 (e.g., to A/D converter 112).

The embodiments described herein provide systems and methods including wireless physical property sensors. Advantages include i) eliminating complicated setup requirements used by at least some known wireless sensor systems, ii) reducing the complexity and cost of an external interrogator compared to LC (inductor-capacitor) resonant frequency-based sensing systems, and iii) reducing susceptibility to communication noise that arises when using analog communications.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other, it is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A physical property sensor comprising:
a sensor coil configured to wirelessly communicate with an external interrogator;
an analog front end communicatively coupled to the sensor coil;
microcontroller communicatively coupled to the analog front end; and
a physical property sensing element, wherein the microcontroller is configured to generate a digitally modulated electrical signal based on signals generated by the physical property sensing element, and wherein the analog front end is configured to forward the digitally modulated electrical signal to the sensor coil for transmission to the external interrogator.

2. The physical property sensor of claim 1, wherein the analog front end comprises an incoming data detection device configured to:
receive data from signals received from the external interrogator; and
provide the received data to the microcontroller for storage.

3. The physical property sensor of claim 1, further comprising a non-volatile memory communicatively coupled to the microcontroller, the non-volatile memory storing data associated with the physical property sensor.

4. The physical property sensor of claim 3, wherein the digitally modulated electrical signal includes the stored data associated with the physical property sensor.

5. The physical property sensor of claim 1, wherein the physical property sensing element is configured to detect at least one of a temperature, a pressure, an SvO2 content, and/or a stress of an environment in which the physical property sensor is located.

6. The physical property sensor of claim 1, wherein the analog front end comprises an energy storage device configured to:
harvest energy from signals received from the external interrogator; and
provide power to the microcontroller using the harvested energy.

7. The physical property sensor of claim 1, further comprising a hermetically sealed housing enclosing the sensor coil, the analog front end, the microcontroller, and at least a portion of the physical property sensing element.

8. The physical property sensor of claim 1, further comprising an analog to digital converter coupled between the microcontroller and the physical property sensing element.

9. A communication system comprising:
an external interrogator; and
a physical property sensor comprising:
a sensor coil configured to wirelessly communicate with the external interrogator;
an analog front end communicatively coupled to the sensor coil;
a microcontroller communicatively coupled to the analog front end; and
a physical property sensing element, wherein the microcontroller is configured to generate a digitally modulated electrical signal based on signals generated by the physical property sensing element, and wherein the analog front end is configured to forward the digitally modulated electrical signal to the sensor coil for transmission to the external interrogator.

10. The communication system of claim 9, wherein the physical property sensor further comprises a non-volatile memory communicatively coupled to the microcontroller, the non-volatile memory storing data associated with the physical property sensor.

11. The communication system of claim 10, wherein the data associated with the physical property sensor includes a sensor ID.

12. The communication system of claim 10, wherein the digitally modulated electrical signal includes the stored data associated with the physical property sensor.

13. The communication system of claim 9, wherein the physical property sensing element is configured to detect at least one of a temperature, a pressure, an SvO2 content, and/or a stress of an environment in which the physical property sensor is located.

14. The communication system of claim 9, wherein the analog front end comprises an energy storage device configured to:
harvest energy from signals received from the external interrogator; and
provide power to the microcontroller using the harvested energy.

15. The communication system of claim 9, wherein the physical property sensor further comprises a hermetically sealed housing enclosing the sensor coil, the analog front end, the microcontroller, and at least a portion of the physical property sensing element.

16. The communication system of claim 9, wherein the physical property sensor further comprises an analog to digital converter coupled between the microcontroller and the physical property sensing element.

* * * * *